(12) United States Patent
Takei et al.

(10) Patent No.: US 8,900,854 B2
(45) Date of Patent: Dec. 2, 2014

(54) LIQUID REFLUX HIGH-SPEED GENE AMPLIFICATION DEVICE

(75) Inventors: Hiroyuki Takei, Kawasaki (JP); Hideyuki Terazono, Kawasaki (JP); Kenji Yasuda, Tokyo (JP)

(73) Assignees: Kanagawa Academy of Science and Technology, Kanagawa (JP); National University Corporation Tokyo Medical and Dental University, Tokyo (JP)

( * ) Notice: Subject to any disclaimer, the term of this patent is extended or adjusted under 35 U.S.C. 154(b) by 164 days.

(21) Appl. No.: 13/138,784
(22) PCT Filed: Mar. 31, 2010
(86) PCT No.: PCT/JP2010/055787
§ 371 (c)(1),
(2), (4) Date: Dec. 5, 2011
(87) PCT Pub. No.: WO2010/113990
PCT Pub. Date: Oct. 7, 2010

(65) Prior Publication Data
US 2012/0077262 A1    Mar. 29, 2012

(30) Foreign Application Priority Data
Mar. 31, 2009  (JP) .................................. 2009-084450

(51) Int. Cl.
*C12M 1/00*  (2006.01)
*C12M 3/00*  (2006.01)
(Continued)

(52) U.S. Cl.
CPC . *B01L 7/52* (2013.01); *F28F 27/02* (2013.01); *B01L 3/50855* (2013.01);
(Continued)

(58) Field of Classification Search
USPC ........................................... 435/283.1–309.4
See application file for complete search history.

(56) References Cited

U.S. PATENT DOCUMENTS 5,508,197 A    4/1996    Hansen et al.
6,533,255 B1 *  3/2003    Mitsuhashi et al. .......... 261/149
(Continued)

FOREIGN PATENT DOCUMENTS

JP    2000-512138 A    9/2000
JP    2001-519224 A    10/2001
(Continued)

OTHER PUBLICATIONS

Choi et al., "Microfluidic system for dielectrophoretic separation based on a trapezoidal electrode array," Lab Chip, 2005, 1161-1167.
(Continued)

Primary Examiner — Nathan Bowers
Assistant Examiner — Lydia Edwards
(74) Attorney, Agent, or Firm — Foley & Lardner LLP

(57) ABSTRACT

The present invention provides a liquid reflux reaction control device comprising:
  a reaction vessel having one or a plurality of wells configured to accommodate a sample;
  a heat exchange vessel provided in contact with the reaction vessel so as to conduct heat to the reaction vessel, and comprising an inlet and an outlet respectively for introducing and draining a liquid of a predetermined temperature;
  a plurality of liquid reservoir tanks provided with a temperature-controllable heat source for maintaining liquids of predetermined temperatures;
  a tubular flow channel that connects the inlet and the outlet of the heat exchange vessel with the liquid reservoir tanks;
  a pump disposed on the tubular flow channel, and configured to circulate the liquid between the heat exchange vessel and the liquid reservoir tank; and
  a switching valve disposed on the tubular flow channel, and configured to control the flow of the circulating liquid, which controls the temperature of the reaction vessel to keep a desired temperature by switching the flows of the liquids of the predetermined temperatures from the plurality of liquid reservoir tanks into the heat exchange vessel at a predetermined time interval,
wherein the amount of the sample is less than or equal to several μL per well, and the total volume of the circulating liquid is more than or equal to several tens of mL per liquid reservoir tank.

27 Claims, 13 Drawing Sheets

(51) Int. Cl.
  *C12M 1/22* (2006.01)
  *B01L 3/00* (2006.01)
  *B01L 7/00* (2006.01)
  *F28F 27/02* (2006.01)
  *F28D 7/00* (2006.01)
  *F28D 15/00* (2006.01)
  *F28D 21/00* (2006.01)

(52) U.S. Cl.
  CPC ....... *B01L 2400/0622* (2013.01); *F28D 7/0008* (2013.01); *B01L 3/50851* (2013.01); *F28D 15/00* (2013.01); *B01L 2300/185* (2013.01); *F28D 2021/0077* (2013.01); *B01L 2400/0633* (2013.01); *B01L 2400/0644* (2013.01)
  USPC .................. 435/289.1; 435/283.1; 435/293.1; 435/293.2; 435/305.2

(56) References Cited

U.S. PATENT DOCUMENTS

| | | | |
|---|---|---|---|
| 2006/0073076 A1 | 4/2006 | Ichiki et al. | |
| 2006/0094108 A1 | 5/2006 | Yoder et al. | |
| 2006/0105433 A1 | 5/2006 | Bickmore et al. | |
| 2006/0139638 A1 | 6/2006 | Muller et al. | |
| 2006/0152708 A1 | 7/2006 | Muller et al. | |
| 2008/0003649 A1* | 1/2008 | Maltezos et al. | 435/91.2 |
| 2008/0102443 A1* | 5/2008 | Fukuda et al. | 435/4 |
| 2008/0124722 A1 | 5/2008 | Dromaretsky et al. | |
| 2010/0190146 A1* | 7/2010 | Bynum et al. | 435/4 |

FOREIGN PATENT DOCUMENTS

| | | |
|---|---|---|
| JP | 2007-110943 A | 5/2007 |
| WO | WO 97/46707 A2 | 12/1997 |
| WO | WO 97/46712 A2 | 12/1997 |
| WO | WO 99/17881 A1 | 4/1999 |
| WO | WO 01/07159 A2 | 2/2001 |
| WO | WO 02/060584 A2 | 8/2002 |
| WO | WO 2004/019033 A1 | 3/2004 |
| WO | WO 2004/070361 A1 | 8/2004 |
| WO | WO 2008/070198 A2 | 6/2008 |

OTHER PUBLICATIONS

Mueller et al., "A 3-D microelectrode system for handling and caging single cells and particles," Biosensors & Bioelectronics, 1999, 14:247-256.

Yasuda, Kenji, "Separation and purification of single cells using on-chip cell sorter," Biomaterials—Seibutsu Zairyo, 2003, 21(2):127-132.

Yasuda, Kenji, Single Cell Handling and Purification Technologies, Nano-biology: Nanotech de Bio o Kaeru, Tan'itsu Sosa, Seisei Gijutsu. Saibo Kogaku, 2006, 25(8):884-888.

Zhang et al., "Dielectrophoresis for manipulation of micro/nano particles in microfluidic systems," Analytical and Bioanalytical Chemistry, 2010, 396(1):401-420.

Terazono et al., "Development of a High-Speed Real-Time Polymerase Chain Reaction System Using a Circulating Water-Based Rapid Heat-Exchange," Japanese Journal of Applied Physics, Jun. 1, 2010, 49(6)6GM05-1 to 06GM05-5.

Wittwer et al., "Continuous Fluorescence Monitoring of Rapid Cycle DNA Amplification," BioTechniques, Jan. 1997, 22:130-138.

* cited by examiner

A

B

A

B

C

A

B

A

B

C

LIQUID REFLUX HIGH-SPEED GENE AMPLIFICATION DEVICE

CROSS-REFERENCE TO RELATED APPLICATIONS

This application is a National Stage application of PCT/JP2010/055787, filed Mar. 31, 2010, which claims priority from Japanese application JP 2009-084450, filed Mar. 31, 2009.

TECHNICAL FIELD

The present invention relates to a gene analysis device using a reaction container, which is suitable for rapidly performing an analysis with a small amount of gene for studies or clinical practice in basic bioscience, basic medical research and medical fields, for example, to a gene analysis using a reaction device for detecting a particular nucleotide sequence at high speed from a nucleic-acid base sequence such as genomic DNA or messenger RNA derived from an animal including human or a plant.

BACKGROUND ART

Polymerase chain reaction (hereinafter, abbreviated as PCR) is a method for amplifying a particular nucleic acid sequence from a mixture of various types of nucleic acids. A particular nucleic acid sequence can be amplified by performing at least one cycle of the following steps: adding into the mixture a DNA template such as genomic DNA or complementary DNA obtained by reverse transcription from messenger RNA, two or more types of primers, thermostable enzymes, salt such as magnesium, and four types of deoxyribonucleoside triphosphates (dATP, dCTP, dGTP and dTTP) and splitting of the nucleic acids; and binding the primers to the nucleic acids; and allowing hybridization using, as a template, the nucleic acids bound by the primers and the thermostable enzymes. Thermal cycling is performed by increasing and decreasing the temperature of a reaction container used for DNA amplification reaction. There are various mechanisms for changing the temperature, including a mechanism in which the temperature of the reaction container containing a sample is changed through heat exchange using a heater, a Peltier element or hot air, a mechanism in which the temperature is changed by alternately bringing the reaction container into contact with heater blocks or liquid baths at different temperatures, and a method in which the temperature is changed by running a sample through a flow channel that has regions of different temperatures. Currently, the fastest commercially available device is, for example, Light Cycler from Roche, which has a mechanism where a specimen, DNA polymerase, small sections of DNA as primers and a fluorescent dye label for measurement are placed into each of a plurality of glass capillary tubes, where the temperatures of small amounts of droplets in the capillary tubes are shifted by blowing hot air at a temperature intended for the droplets, for example, at two temperatures, i.e., 55° C. and 95° C., while at the same time, the glass capillary tubes are irradiated with light for exciting the fluorescent dye to measure the resulting fluorescent intensity. According to these methods, the temperature of the sample can be repeatedly shifted.

Moreover, a fluid impingement thermal cycler device has been reported that controls the temperature of a specimen by impingement of fluid jet on the outer wall of the specimen-containing region (Japanese Patent Publication No. 2001-519224 (Patent Document 1)).

PRIOR ART DOCUMENTS

Patent Documents

[Patent Document 1] Japanese Patent Publication No. 2001-519224

SUMMARY OF THE INVENTION

Problem to be Solved by the Invention

A temperature rate obtained with a heater or a Peltier element is as slow as about a few ° C. per second, and they have difficulty in shifting the temperature without overshoot in the temperature. Basically, when conduction through a solid substance is utilize, a heat gradient is generated between the heat source and the surface thereof, rendering strict control of the temperature impossible. Furthermore, since heat is lost as soon as the sample touches the heater or the Peltier element, delay occurs until the surface restores the predetermined temperature. Moreover, bringing a reaction vessel into contact with a separate heater or liquid bath is associated with complication in the transfer mechanism and difficulty in controlling the temperature of the heater or the liquid vessel. Further, with a method in which a sample is fed into a flow channel having different temperature regions, problems arise that the surface temperature of the flow channel itself changes with the movement of the sample, and thus it becomes difficult to control the temperature. When the temperature is shifted by blowing hot air, the small heat capacity of the air requires a large amount of air to be blown. Similarly, since the heat capacity of the air is small, it is difficult to control the eventual blowing temperature of the air in precise increments of 1° C. using an electrically-heated wire or the like.

Thus, the present invention has an objective of providing a reaction control device that is capable of conducting accurate temperature control, temperature measurement and rapid increase and decrease in the temperature. More specifically, the present invention has an objective of providing a DNA amplification device that is capable of conducting accurate temperature control, temperature measurement and rapid increase and decrease in the temperature, so as to carry out PCR reaction at high speed, with high accuracy and high amplification rate.

Means for Solving the Problem

In order to accomplish the above-described objective, a reaction control device of the present invention is characterized by: using, as media for heat exchange, liquids having a large heat capacity and maintaining respective temperatures for shifting the temperature of a sample solution; using means for shifting the plurality of liquids having large heat capacities and different temperatures at high speed; and using a minute reaction vessel in which rapid heat exchange is conducted between the liquids with large heat capacities and the sample solution. Specifically, a minute reaction vessel having a structure and a material suitable for heat exchange; a heat exchange vessel for circulating the liquids at temperatures appropriate for each reaction outside the minute reaction vessel; a plurality of liquid reservoir tanks including a heat source for maintaining the temperatures of the liquids with high accuracy; a switching valve system for guiding a liquid from any liquid reservoir tank to the exterior of the reaction vessel so as to rapidly shift the temperature of the minute reaction vessel; and a mechanism configured to prevent liquids of different temperatures from being mixed upon switching the valve system.

Thus, the present invention provides the following liquid reflux reaction control device.

(1) A liquid reflux reaction control device comprising:
a reaction vessel having one or a plurality of wells configured to accommodate a sample;
a heat exchange vessel provided in contact with the reaction vessel so as to conduct heat to the reaction vessel, and comprising an inlet and an outlet respectively for introducing and draining a liquid of a predetermined temperature;
a plurality of liquid reservoir tanks provided with a temperature-controllable heat source for maintaining liquids of predetermined temperatures;
a tubular flow channel that connects the inlet and the outlet of the heat exchange vessel with the liquid reservoir tanks;
a pump disposed on the tubular flow channel, and configured to circulate the liquid between the heat exchange vessel and the liquid reservoir tank; and
a switching valve disposed on the tubular flow channel, and configured to control the flow of the circulating liquid, wherein said switching valve controls the temperature of the reaction vessel to keep a desired temperature by switching the flows of the liquids of the predetermined temperatures from the plurality of liquid reservoir tanks into the heat exchange vessel at a predetermined time interval,
wherein the amount of the sample is less than or equal to several μL per well, and the total volume of the circulating liquid is more than or equal to several tens of mL per liquid reservoir tank.

(2) The liquid reflux reaction control device according to (1) above, which is used as a PCR device.

(3) The liquid reflux reaction control device according to either one of (1) and (2) above, further comprising, where a fluorescent dye is added to the sample, a fluorescent detector configured to detect fluorescence emitted from the fluorescent dye in the well in conjunction with switching the temperature of the reaction vessel and measure the change in the fluorescent intensity with time.

(4) The liquid reflux reaction control device according to (3) above, wherein the fluorescent detector is disposed in correspondence with each of the wells of the reaction vessel.

(5) The liquid reflux reaction control device according to either one of (3) and (4) above, further comprising:
means for estimating the change in a temperature of a sample solution based on the change in the fluorescent intensity of the sample solution in one or a plurality of wells of the reaction vessel; and
means for rapidly shifting the temperature of the reaction vessel based on the result thereof.

(6) The liquid reflux reaction control device according to any one of (1) to (5) above, wherein the number of the liquid reservoir tanks is the same as the number of temperatures intended for the reaction vessel.

(7) The liquid reflux reaction control device according to (6) above, wherein the number of the liquid reservoir tanks is 2 or 3.

(8) The liquid reflux reaction control device according to any one of (1) to (7) above, wherein the bottom and wall surfaces of the reaction vessel is formed of a metal including aluminum, nickel, magnesium, titanium, platinum, gold, silver or copper, or silicon having a thickness of 1-100 microns.

(9) The liquid reflux reaction control device according to any one of (1) to (8) above, wherein the shape of the bottom surface of the well is flat, hemispherical, trigonal pyramid shape or spherical.

(10) The liquid reflux reaction control device according to any one of (1) to (9) above, wherein a reagent necessary for the reaction is accommodated in each of the wells in a dry form in advance such that it eluted and brought into reaction upon contacting with the sample solution.

(11) The liquid reflux reaction control device according to any one of (1) to (10) above, wherein the reaction vessel further comprises an aperture or an optical window that facilitates measurement of an optical signal from the sample in the reaction vessel.

(12) The liquid reflux reaction control device according to any one of (1) to (11) above, wherein the reaction vessel is provided in a removable manner with respect to the heat exchange vessel.

(13) The liquid reflux reaction control device according to (12) above, wherein the reaction vessel is provided in a removable manner with respect to the heat exchange vessel in one of the following fashion:
(a) a cylindrical casing is provided surrounding the reaction vessel, and a cylindrical reaction vessel socket is provided on the heat exchange vessel, while the outer surface of the casing of the reaction vessel and the inner surface of the reaction vessel socket of the heat exchange vessel are threaded so that the reaction vessel is removably attached to the heat exchange vessel through rotation movement along the thread;
(b) a cylindrical casing surrounding the reaction vessel and a cylindrical reaction vessel socket of the heat exchange vessel are tapered with respect to each other so as to be removably attached to each other by pressing the reaction vessel against the reaction vessel socket;
(c) the reaction vessel is secured to a glass-slide like reaction vessel casing while the reaction vessel socket of the heat exchange vessel is provided with a guide rail so that the glass-slide like reaction vessel casing is removably attached to the socket along the guide rail; and
(d) the glass-slide like reaction vessel casing is inserted into a slide holder with a hinge mechanism so that the glass-slide like reaction vessel casing is removably attached to the reaction vessel socket of the heat exchange vessel through rotation movement of the hinge mechanism.

(14) The liquid reflux reaction control device according to either one of (12) or (13) above, further comprising a mechanism that allows the reaction vessel to attach to or remove from the heat exchange vessel during reflux of the liquid without leaking the liquid out from the liquid reflux reaction control device.

(15) The liquid reflux reaction control device according to any one of (1) to (14) above, wherein the liquid reservoir tank is provided with a heat source, a thermometer and a liquid stirrer, wherein the liquid stirrer is provided with a heat source controller that can control the temperature distribution of the liquid in the liquid reservoir tank within 5° C. by stirring the liquid in the liquid reservoir tank continuously or at a duty cycle ratio of 10% or higher.

(16) The liquid reflux reaction control device according to any one of (1) to (15) above, further comprising a switching valve control mechanism configured to control the switching valve.

(17) The liquid reflux reaction control system according to any one of (1) to (16) above, wherein the switching valve can lead the liquid in any liquid reservoir tank among the plurality of liquid reservoir tanks to the heat exchange vessel, and return the liquid in the heat exchange vessel to the original liquid reservoir tank.

(18) The liquid reflux reaction control device according to either one of (16) and (17) above, wherein, when the liquid in the heat exchange vessel is replaced by controlling the switching valve, the switching valve is controlled such that the liquid in the heat exchange vessel is led to a liquid reservoir tank maintained at a temperature closest to the temperature of the liquid.

(19) The liquid reflux reaction control device according to any one of (1) to (18) above, further comprising an auxiliary temperature control mechanism comprising a thermal insulator, a heater and a cooling mechanism, wherein the mechanism suppresses the fluctuation of the temperature of the liquid in the flow channel that connects the switching valve to the liquid reservoir tank.

(20) The liquid reflux reaction control device according to any one of (1) to (19) above, further comprising in the switching valve a mechanism configured to control the shift in the temperature by continuously replacing the liquid from the liquid reservoir tank regardless of whether or not the liquid in the flow channel connecting the switching valve to the liquid reservoir tank is led to the heat exchange vessel.

(21) The liquid reflux reaction control device according to any one of (1) to (20) above, wherein the switching valve comprises a piston that slides in a hollow structure having a circular or polygonal cross-section so as to control the temperature of the liquid that is in contact with the reaction vessel according to the position of the piston.

(22) The liquid reflux reaction control device according to (21) above, wherein the piston in the switching valve slides by:
    (a) mechanically applying external force to the piston rod connected to the piston;
    (b) using a piston that is a magnetic body itself or a piston mounted with a magnetic body inside to utilize interaction between the piston and a magnetic field generation mechanism including an electromagnetic coil arranged outside the switching valve; or
    (c) generating difference in pressure due to the flow of the liquids circulating at both ends of the piston.

(23) The liquid reflux reaction control device according to any one of (1) to (20) above, wherein, in the switching valve,
    a cylindrical, discoid or conical rotor that is rotatably inserted into the heat exchange vessel, wherein said rotor comprises a plurality of grooves formed in its outer surface as flow channels for the liquid delivered from the liquid reservoir tank, and a tunnel-like flow channel connected to each of the grooves to allow fluid communication,
    both ends of the tunnel-like flow channel serve as an inlet or an outlet of the switching valve, and
    rotation of the rotor allows liquids at different temperatures to be introduced into the inlet to make contact with exterior of the reaction vessel upon passing the groove part.

(24) The liquid reflux reaction control device according to any one of (1) to (23) above, wherein the circulating liquid used is a liquid with a large heat capacity and low viscosity.

(25) The liquid reflux reaction control device according to any one of (1) to (24) above, wherein the circulating liquid used is a liquid having a boiling point higher than that of water.

(26) The liquid reflux reaction control device according to any one of (1) to (25) above, wherein the circulating liquid used is a liquid having a freezing point lower than that of water.

(27) The liquid reflux reaction control device according to (1) above, further comprising a mechanism configured to prevent the sample from evaporating, the mechanism comprising:
    a member that sealingly covers the surface of the reaction vessel having the well, such that at least part of it is optically transparent so as to allow optical observation of the sample solution in the well; and
    a heating mechanism configured to heat a part of the optically transparent part of the member.

(28) The liquid reflux reaction control device according to (27) above, wherein the distance between the optically transparent part of the member and the surface of the reaction vessel having the well is less than or equal to 3 mm.

(29) The liquid reflux reaction control device according to (27) above, wherein the temperature of the optically transparent part of the member is heated with the heating mechanism in a range of 80° C. to 110° C.

Advantageous Effects of the Invention

Examples of advantages of the present invention for controlling the temperature of a reaction vessel with refluxing liquids include the following. First, the problem of a temperature overshoot can be solved. Specifically, since a temperature of a constantly refluxing liquid is almost constant, the temperature of the surface of a reaction vessel and the temperature of the liquid can be equilibrated almost at once. According to the present invention, heat capacities of the reaction vessel and the sample are insignificant as compared to that of the refluxing liquid. Moreover, even when some heat is lost from a part the liquid, essentially no heat gradient is caused since the liquid is continuously flowing. Of course, the temperature of the reaction vessel does not exceed the temperature of the liquid. According to a typical embodiment of the present invention, liquids of different temperatures can sequentially be run into the heat exchange vessel so as to shift the temperature by 30° C. or higher within 0.5 seconds. Hence, according to the present invention, time required for shifting the temperature can be made extremely short and, for example, total time for conducting PCR reaction can be made dramatically shorter than the time required with a conventional device.

In a reaction control device according to the present invention, a liquid kept at a constant temperature is brought into contact with the exterior of a reaction vessel having good heat conductivity, and thereafter the liquid is rapidly replaced with a liquid at different temperature, so that rapid increase and decrease in the temperature of a sample can be realized and controlled with high accuracy. According to the present invention, PCR reaction can be conducted at high speed, with high accuracy and at high amplification rate.

In addition, since the present invention is capable of preventing a sample solution from evaporating due to heating of the sample solution, it is advantageous in PCR reaction that uses a small amount of sample.

EMBODIMENTS FOR CARRYING OUT THE INVENTION

Hereinafter, embodiments of the present invention will be described with reference to the drawings although these embodiments are provided for illustration only and do not limit the scope of the present invention.

Figure 1:
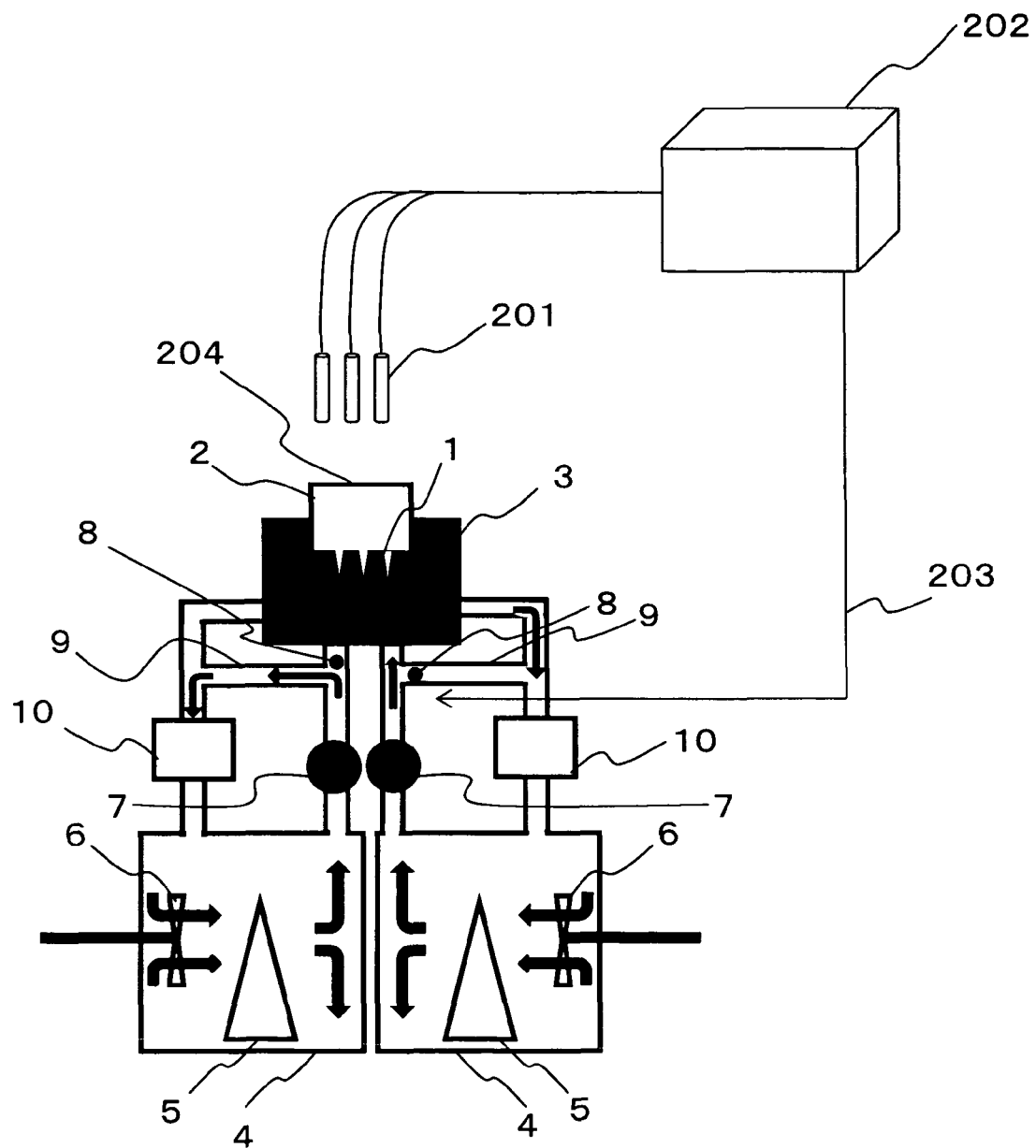
FIG. 1 A schematic view showing a general structure of a reaction control device of the present invention.

FIG. 1 is a schematic view showing a general structure of one embodiment of a reaction control device of the present invention. Typically, a reaction control device of the present invention comprises a reaction vessel 1, a reaction vessel casing 2, a heat exchange vessel 3, liquid reservoir tanks 4, heat sources 5, stirring mechanisms 6, pumps 7, switching valves 8, bypass flow channels 9 and auxiliary temperature control mechanisms 10. Preferably, the reaction control device of the present invention further comprises fluorescence detectors 201, a control analyzer 202 for transmitting a control signal 203 and an optical window (or aperture) 204.

The reaction vessel 1 may typically be composed of a thin plate of a metal such as aluminum, nickel, magnesium, titanium, platinum, gold, silver and copper or silicon, with a plurality of wells. It is, however, not limited to these materials as long as the material has high heat conductivity and does not interfere with PCR. Alternatively, the surface of a thin metal membrane may be covered with a hydrophilic material such as plastic that prevents corrosion of the metal. The thickness of the thin plate at the well region is preferably thinner than the surrounding area in order to increase the heat conductivity, and it is typically, but not limited to, a thickness of about 10 to 30 microns. The region between the adjacent wells is preferably thicker in order to maintain the overall strength, and it is typically in a range of, but not limited to, 100 microns to 500 microns. The reaction vessel 1 is typically secured to a square, circular or other bottom surface of the reaction vessel casing 2 to be formed integrally. Typically, the reaction vessel 1 and the reaction vessel casing 2 are removable with respect to the heat exchange vessel 3 (see FIG. 4).

A liquid used for heat exchange is introduced into the heat exchange vessel 3. The temperature of the introduced liquid is controlled by the heat source 5 disposed inside the liquid reservoir tank 4. In order to even the temperature inside the liquid reservoir tank 4 by rapidly conducting heat away from the surface of the heat source 5, the stirring mechanism 6 is preferably provided. The liquid in the liquid reservoir tank 4 is led inside the flow channel with the pump 7. In accordance with the switching valve 8, the liquid is led to the heat exchange vessel 3 or directly returns to the liquid reservoir tank 4 through the bypass flow channel 9. If necessary, the auxiliary temperature control mechanism 10 can delicately control the temperature of the liquid so as to suppress the temperature fluctuation inside the liquid reservoir tank 4.

A liquid introduced into the heat exchange vessel 3 may be, but not limited to, water, and any liquid can be used as long as it has large heat capacity and low viscosity (e.g., liquid ammonia). For example, a liquid having a higher boiling point than water can be used to ensure a sample solution of 100° C., or a liquid having a lower freezing point than water can be used to ensure temperature shift to the freezing point of water while preventing solidification of the liquid circulating within the device.

Preferably, as shown in FIG. 1, the reaction vessel casing 2 is provided with the optical window 204 that allows transmission of light for exciting a fluorescent dye and fluorescence therefrom such that change in the fluorescent intensity of the fluorescent dye in a sample solution that alters according to the reaction of the sample solution in the reaction vessel 1 can be measured for one or each of the plurality of reaction vessels. In addition, arrangement of the fluorescence detectors 201 allows measurement of fluorescent intensity in the reaction vessel 1 with time. According to the example shown in FIG. 1, an excitation light irradiation mechanism and a fluorescence detecting mechanism are provided in each of the plurality of fluorescence detectors 201. This structure allows, for example, independent measurement of different PCR amplification information of a plurality of reaction vessels 1 having different primers or different sample solutions upon PCR reaction. In addition, the fluorescent intensity data acquired with the fluorescence detector 201 is recorded with the control analyzer 202, which has a function of estimating the amount of DNA or mRNA in the sample solution obtained by the PCR reaction. Moreover, the control analyzer 202 also has a function of estimating whether or not the temperature of the sample solution has reached the intended temperature after valve switching based on the change in the fluorescent intensity with time by acquiring switching information of the switching valve 8, and also has a mechanism configured to control the valve switching based on that result. This is estimated by a decrease in the amount of change or elimination of the fluorescent intensity with unit time while the mobility of water molecules that are universally possessed by a fluorescent dye is exploited in view that fluorescence quenching depends on the temperature of a liquid, and this is particularly effective for confirming achievement of a high temperature state that results in DNA denaturation.

According to the example shown in FIG. 1, detectors are provided one for each reaction vessel 1. Alternatively, a light source for exciting fluorescence can be combined with a camera capable of quantitating and detecting fluorescence such as a cooled CCD camera to measure the change in the fluorescent intensity of the plurality of reaction vessels 1. Alternatively, when the number of detectors used is less than the number of the reaction vessels 1, a mechanical driving mechanism capable of travelling on the X-Y plane at high speed can be combined with the detectors so as to measure the fluorescent intensities of all of the reaction vessels 1.

The volume of the sample solution is usually less than or equal to several μL per well, but it may be used in a range of 0.1 μL to 100 μl, per well, preferably 0.5 μL to 10 μL per well, more preferably 1 μL, to 10 μL per well, still more preferably 1 μL to 5 μL per well and most preferably 1 μL to 2 μL per well. Besides the sample solution, a mineral oil or the like for preventing evaporation of the sample solution may also be contained in the well. The volume of the mineral oil is preferably, but not limited to, about several μL (e.g., 3 to 4 μL), and obviously appropriately changeable by those skilled in the art according to the size of the well or the amount of the sample.

Figure 2:
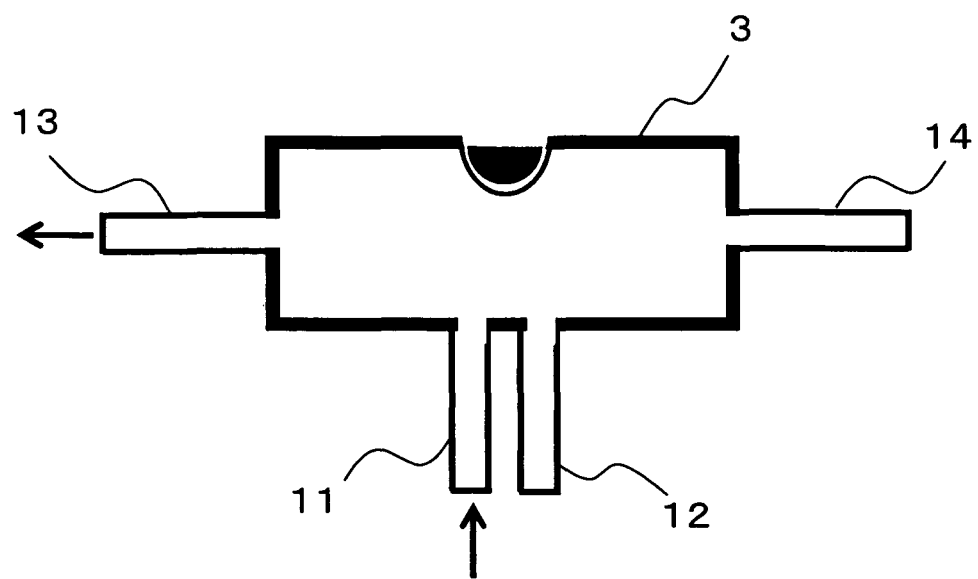
FIG. 2 An outline view of a heat exchange vessel used in a reaction control device of the present invention.
Figure 2:
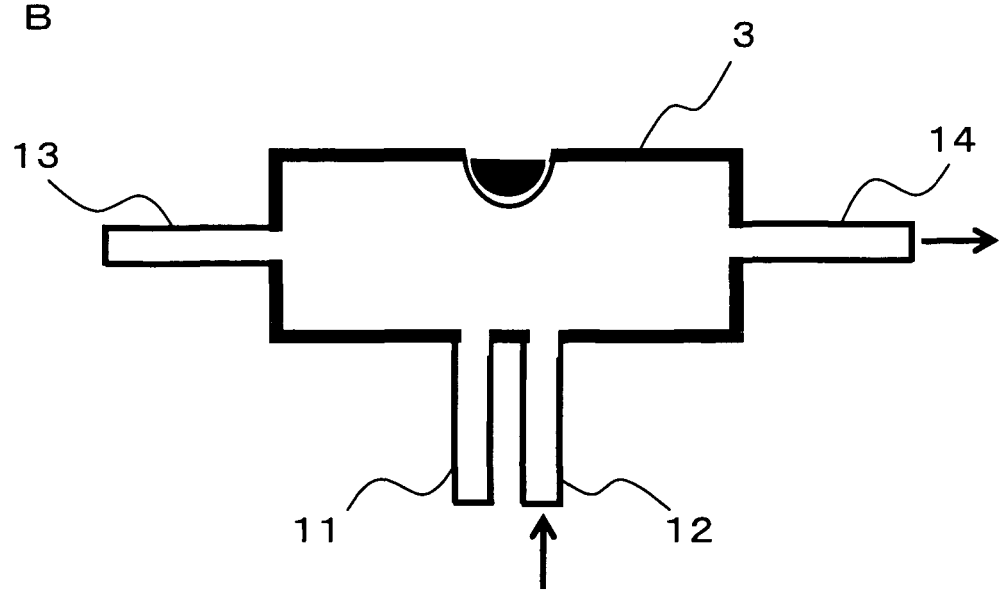

FIG. 2 is an outline view of the heat exchange vessel 3 used in the reaction control device of the present invention. As basic configuration, the heat exchange vessel 3 is provided with inlets A (11) and B (12) for introducing liquids at different temperatures. The heat exchange vessel 3 is also provided with a plurality of outlets, i.e., outlets A (13) and B (14), for returning the liquid from the heat exchange vessel 3 to the liquid reservoir tank 4. FIG. 2A schematically shows introduction and discharge of a liquid at a certain temperature from the liquid reservoir tank 4 through the inlet A (11) and the outlet A (13), respectively, while FIG. 2B schematically shows introduction and discharge of a liquid at a different temperature from the liquid reservoir tank 4 through the inlet B (12) and the outlet B (14), respectively. The number of the inlets is not limited to two, and multiple inlets may be provided as much as the number that matches the number of the temperatures of the sample solution to be shifted. For example, in order to realize a three-temperature system, the number of inlets would be three. Similar to the case of inlets, the number of the outlets is also not limited to two. Here, the arrows in FIG. 2 briefly indicate the flowing direction of the liquid introduced into or discharged from the heat exchange vessel 3.

A total volume of a liquid circulating between the heat exchange vessel 3 and the liquid reservoir tank 4 is generally more than or equal to several tens of mL, preferably more than or equal to 100 mL, more preferably more than or equal to 200 mL, and most preferably more than or equal to 300 mL considering the heat capacity and the temperature stability of the liquid. The upper limit of the volume may appropriately be determined in consideration of the portability of the device or the like.

The volume of the heat exchange vessel 3 is preferably about 10 times or more, more preferably about 100 times or more and most preferably about 1000 times or more the amount of the sample per well. Typically, the volume of the heat exchange vessel is about 0.01 mL to 10 mL, more preferably about 0.05 mL to 5 mL and most preferably about 0.1 mL to 2 mL per well.

Figure 3:
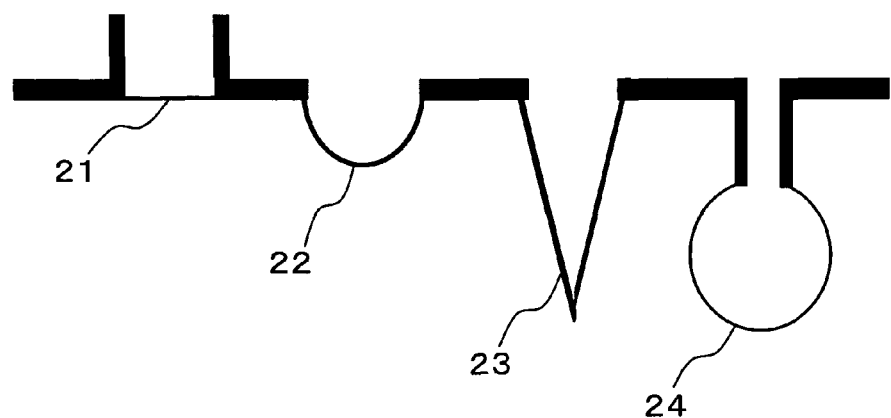
FIG. 3 A schematic view showing embodiments of a reaction vessel used in a reaction control device of the present invention and illustrating a method for dissolving a lyophilized reagent.
Figure 3:
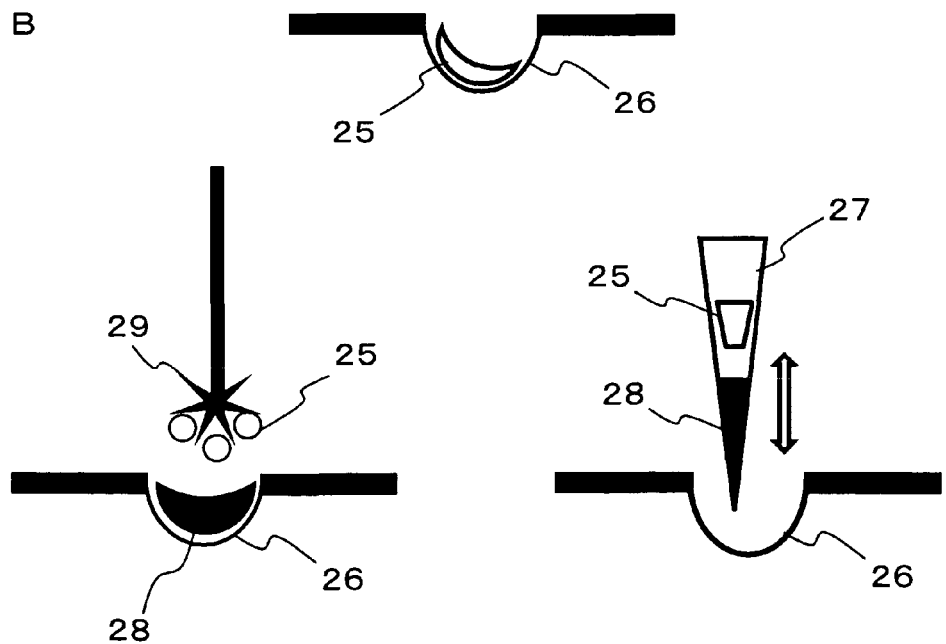

FIG. 3 is a schematic view showing an embodiment of a reaction vessel used in a reaction control device of the present invention and a method for dissolving a lyophilized reagent. Reaction vessels or wells in various shapes can be used while FIG. 3A shows examples where the surface of the heat exchange vessel that makes contact with a liquid is flat (reaction vessel A (21)), hemispherical (reaction vessel B (22)), a trigonal pyramid shape (reaction vessel C (23)) or spherical (reaction vessel D (24)). In terms of the efficiency of heat conduction, those skilled in the art would readily understand that the area of the surface of the heat exchange vessel that makes contact with a liquid is preferably larger for better efficiency.

Conveniently, the reagent necessary for reaction is lyophilized. As can be appreciated from FIG. 3B, a lyophilized reagent 25 can be prepared and placed in the bottom of the reaction vessel 26. Alternatively, a plug-shaped lyophilized reagent 25 may be provided inside a dispensing chip 27 used for dispensing the sample so that the reagent can be dissolved in the sample by shaking the sample solution 28 up and down. Alternatively, a lyophilized reagent 25 can be provided on a surface of a fiber ball 29 made of a bundle of nylon fibers or the like so that the lyophilized reagent is dissolved by inserting and stirring the fiber ball in a sample 28 in the reaction vessel 26.

Figure 4:
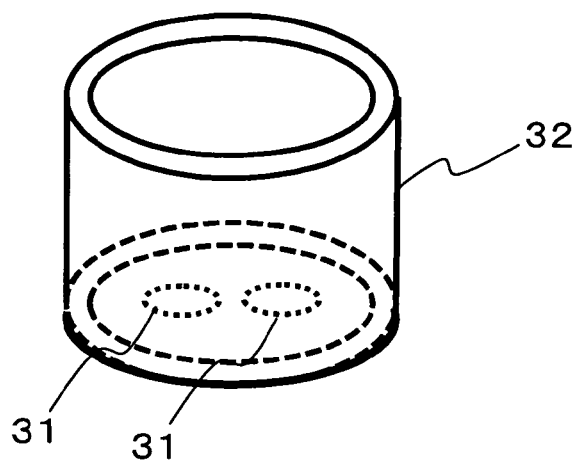
FIG. 4 A schematic view showing a cylindrical reaction casing used in a reaction control device of the present invention and illustrating methods for attaching it to a heat exchange vessel.
Figure 4:
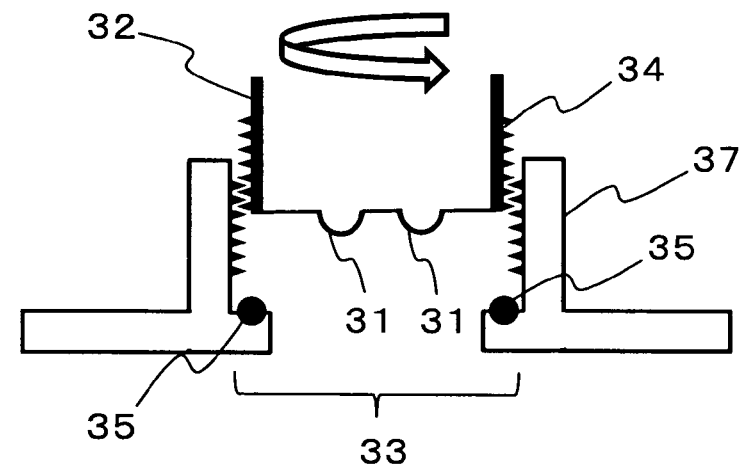
Figure 4:
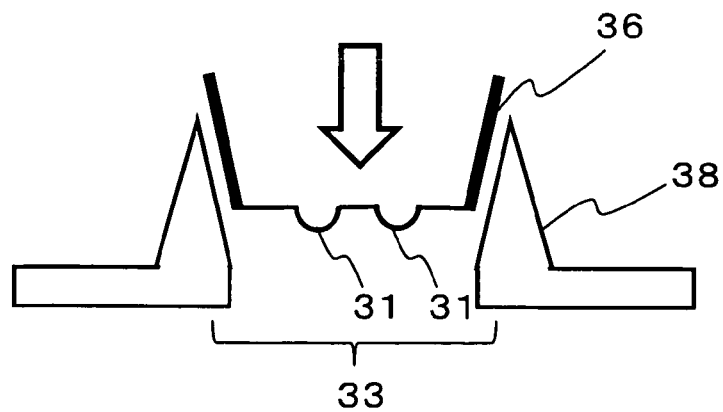

FIG. 4 is a schematic view showing a cylindrical reaction casing 32 used in a reaction control device of the present invention, and illustrating a method for attaching the cylindrical reaction casing 32 to a heat exchange vessel 37. Since directly handling a reaction vessel made from a thin membrane is inconvenient, a reaction vessel 31 is conveniently secured to the reaction vessel casing 32 as shown in FIG. 4A. The reaction vessel casing 32 is preferably formed of a heat insulating material such as polystyrene, polycarbonate, PEEK, acrylic or the like. In addition, the area of the connection with the reaction vessel 31 is desirably kept as small as possible (e.g., 5 mm$^2$ or smaller) for rapid and highly accurate increase and decrease in the temperature of the reaction vessel 31.

FIG. 4B shows, as one embodiment for attaching the reaction vessel 31 to the heat exchange vessel 37, a method in which a thread 34 is formed in the surface of the reaction vessel casing 32 so as to screw the reaction vessel casing 32 in the reaction vessel socket 33 of the heat exchange vessel 37. With reference to FIG. 4B, the opening is preferably provided with a seal 35 in order to maintain water tightness. FIG. 4C shows other method for attaching the reaction vessel 31 to the heat exchange vessel 37. Referring to FIG. 4C, a tapered reaction vessel casing 36 can be employed for attachment to the heat exchange vessel 38 by pressure only.

Figure 5:
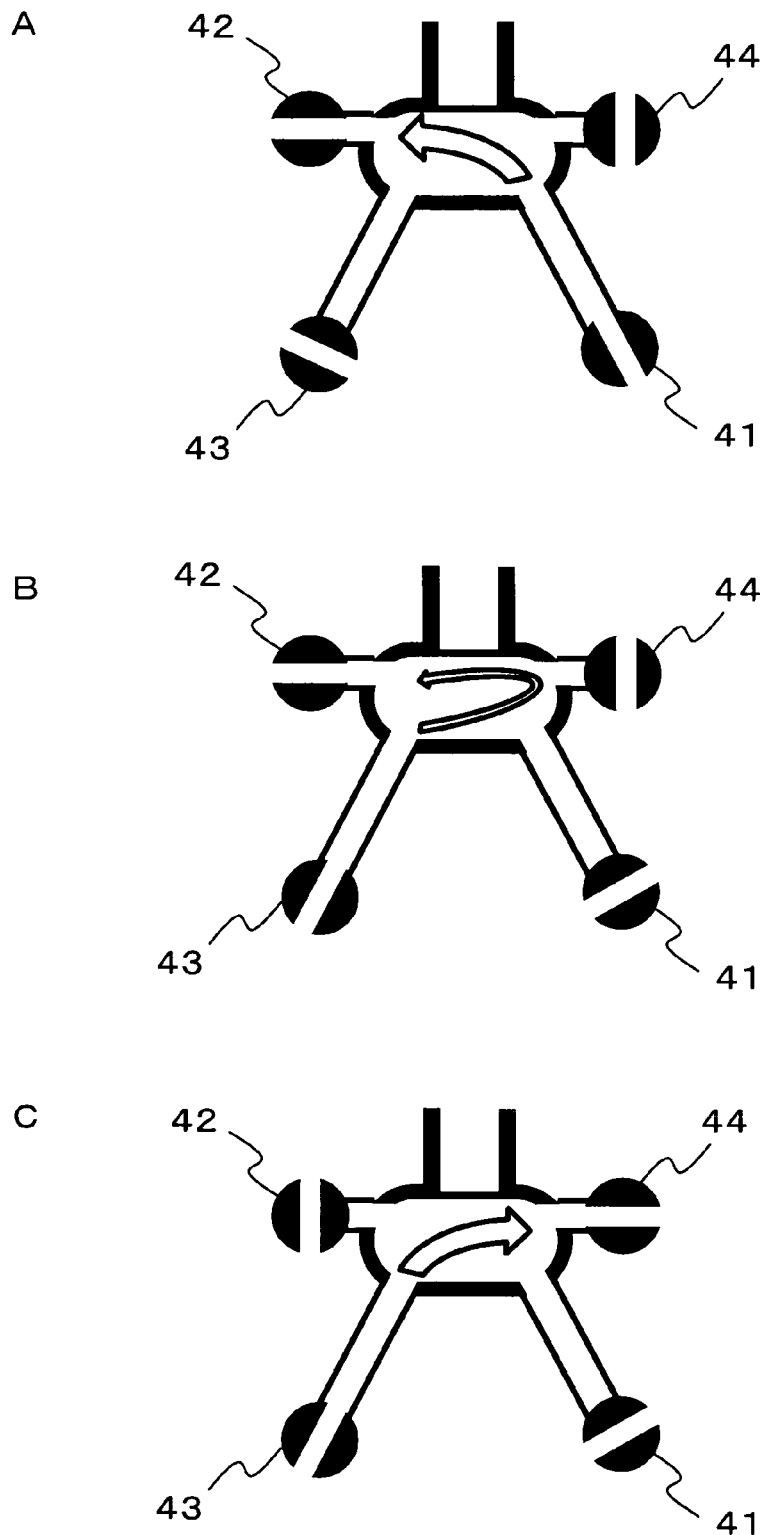
FIG. 5 A schematic view showing a sequence of switching a valve used for a reaction control device of the present invention.

FIG. 5 shows specific examples of a switching mechanism of a valve used in a reaction control device of the present invention, where inlet valves A (41) and B (43) for introducing a liquid into a reaction vessel and outlet valves A (42) and B (44) for leading the liquid outside are shown. A liquid led in from the inlet valve A (41) returns to the liquid reservoir tank 4 via the outlet valve A (42) whereas a liquid led in from the inlet valve A (43) returns to a different liquid reservoir tank 4 via the outlet valve B (44). By alternately switching these two states, the sample in the reaction vessel can be brought into reaction. According to a more desirable valve switching method, other than the above-described two states, the inlet valve B (43) and the outlet valve A (42) or the inlet valve A (41) and the outlet valve B (44) are released at the same time for a moment so that the liquids at different temperatures can be prevented from mixing with each other, thereby facilitating the temperature control of the liquid reservoir tank in each system.

A circulating rate of a liquid is not particularly limited, but generally about 1 mL/second to 100 mL/second, more preferably 5 mL/second to 50 mL/second and most preferably 7 mL/second to 15 mL/second.

Figure 6:
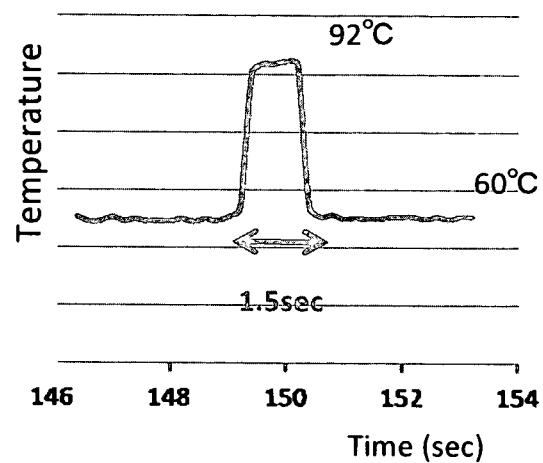
FIG. 6 Diagrams showing (A) data with respect to the shift in the temperature and (B) results from PCR reaction, using a reaction control device of the present invention.
Figure 6:
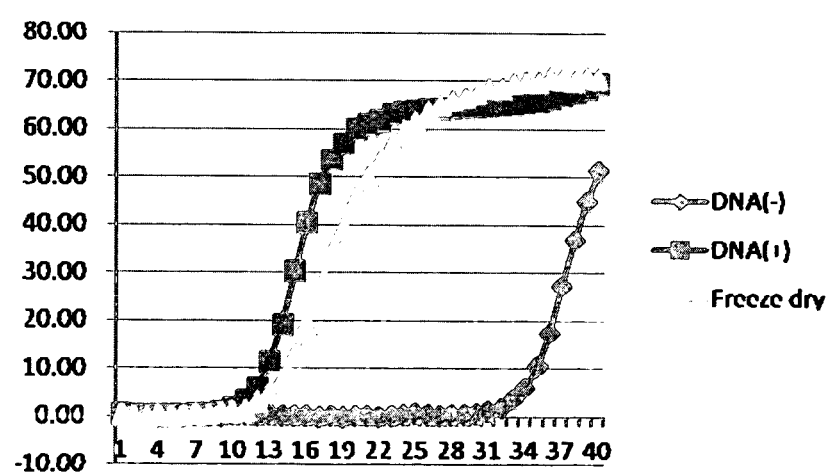

FIG. 6A is a graph obtained from data of temperature control realized by using the above-described mechanism. As can be appreciated from FIG. 6A, the temperature can be increased from 60° C. to 92° C. and decreased to 60° C. within a short time of 1.5 seconds. FIG. 6B is a graph showing the results from real-time PCR. The conditions of the solution upon carrying out PCR were as follows. The followings were mixed in the indicated proportion: 1.0 μL of reaction buffer, 1

μL of 2 mM dNTP (dATP, dCTP, dGTP, dTTP), 1.2 μL of 25 mM magnesium sulfate, 0.125 μL of 10% fetal bovine serum, 0.5 μL of SYBR Green I, 0.6 μL each of two types of primers, 3.725 μL of sterile water, 0.25 μL of KOD plus polymerase and 1.0 μL of genomic DNA. Temperature conditions were first 95° C. for 10 seconds, then 40 cycles of temperature alteration at 95° C. for 1 second and 60° C. for 3 seconds. The circulating rate of the liquid was about 10 mL/second.

Figure 7:
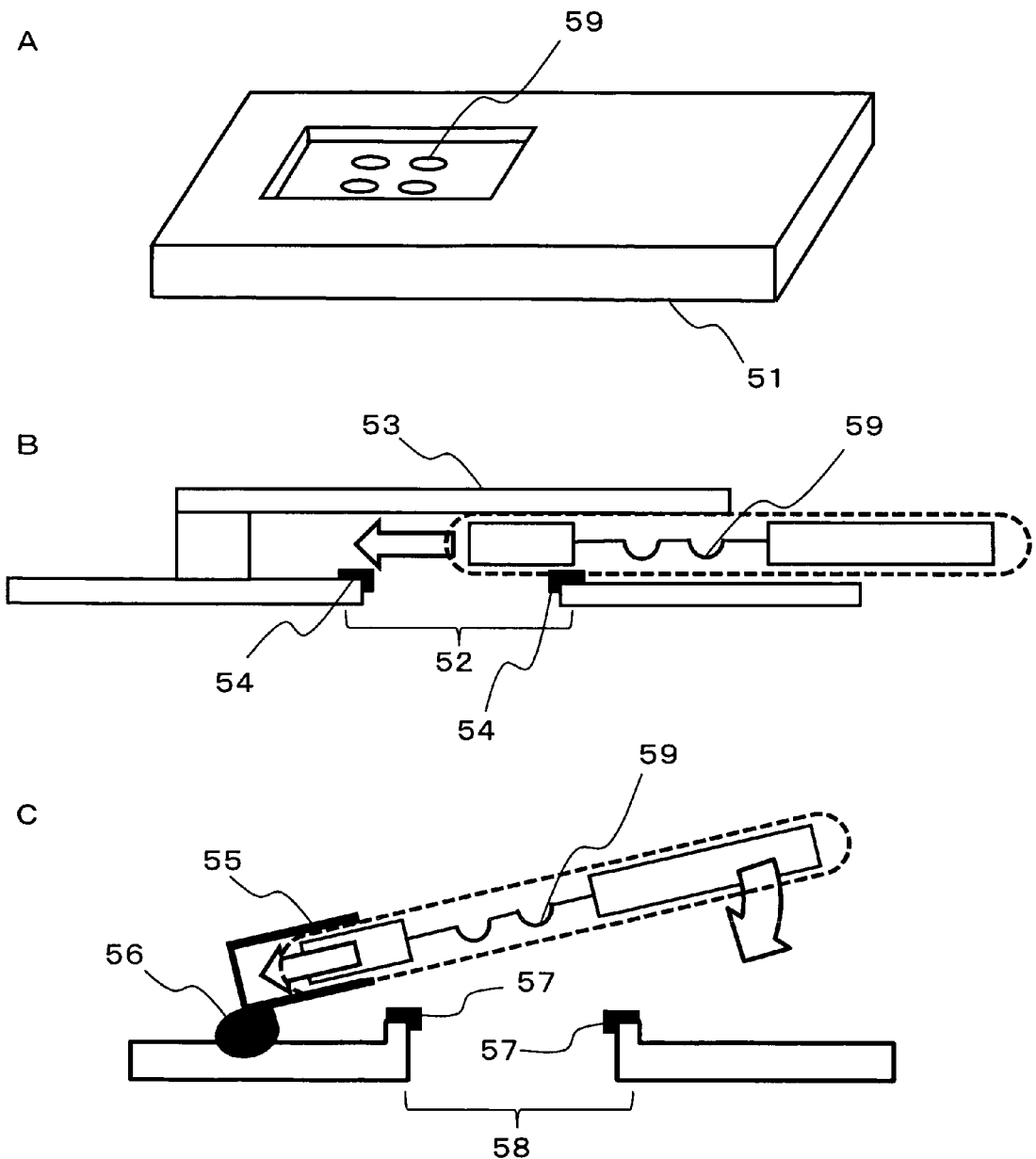
FIG. 7 A schematic view showing methods for attaching a glass-slide like reaction casing used in a reaction control device of the present invention to the heat exchange vessel.

FIG. 7 shows variations of methods for attaching a reaction vessel 59 and a reaction vessel casing 51 used in the reaction control device of the present invention to the heat exchange vessel. The reaction vessel 59 is held and attached to the glass-slide like reaction vessel casing 51 (FIG. 7A). In order to attach this glass-slide like reaction vessel casing 51 to the heat exchange vessel, the reaction vessel casing 51 can transversely slide along a guide rail 53 and pressed against a seal 54 for fixation (FIG. 7B). Alternatively, the glass-slide like reaction casing 51 can be inserted into a slide socket 55 and pressed against a seal 57 utilizing a hinge 56 (FIG. 7C).

Figure 8:
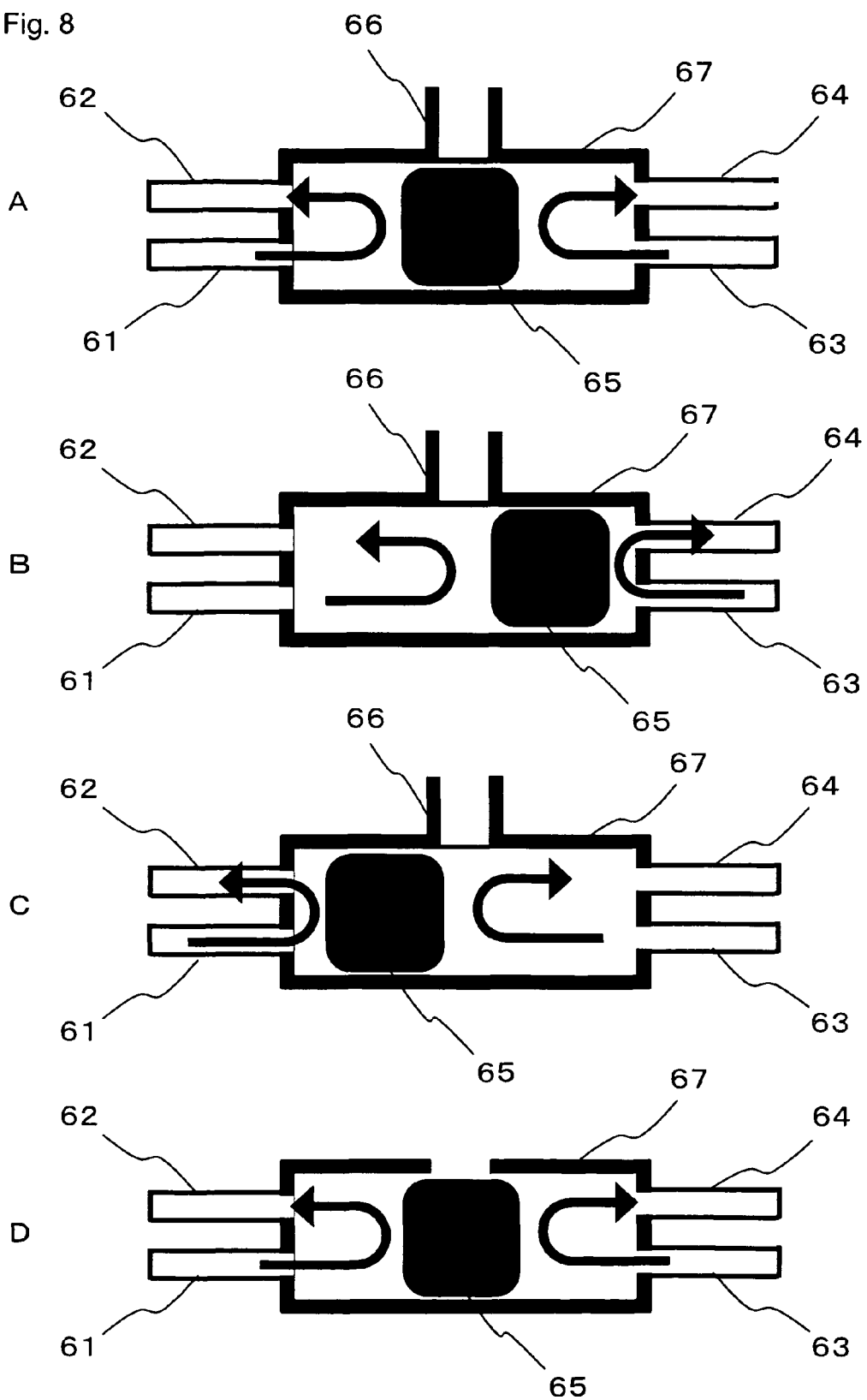
FIG. 8 A schematic view showing a driving mechanism for a slide piston valve used in a reaction control device of the present invention.

FIG. 8 gives schematic views showing variations of switching mechanisms of a valve used in a reaction control device of the present invention, having a driving mechanism with a slide piston valve different from that shown in FIG. 5. A piston 65 that can transversely slide is used as a valve mechanism for shifting the temperature of a reaction vessel 66. On the left side of the piston 65, a liquid is introduced into a heat exchange vessel 67 via an inlet A (61) and led outside via an outlet A (62). On the right side of the piston 65, a liquid is introduced into the heat exchange vessel 67 via an inlet B (63) and led outside via an outlet B (64). When the piston 65 slides to the right with respect to the reaction vessel 66, the temperature of the reaction vessel 66 comes to equilibrium with that of the liquid introduced via the inlet A (61). On the other hand, when the piston 65 slides to the left, the reaction vessel 66 comes to equilibrium with the temperature of the liquid introduced via the inlet B (63). When the piston 65 is positioned right below the reaction vessel 66, the reaction vessel 66 can be removed without leakage of the liquid. The piston 65 is preferably prepared from a material with good heat insulation, or has a hollow inside filled with a gas or in vacuum state. Here, the arrows in FIG. 8 briefly indicate flow directions of the liquid.

Figure 9:
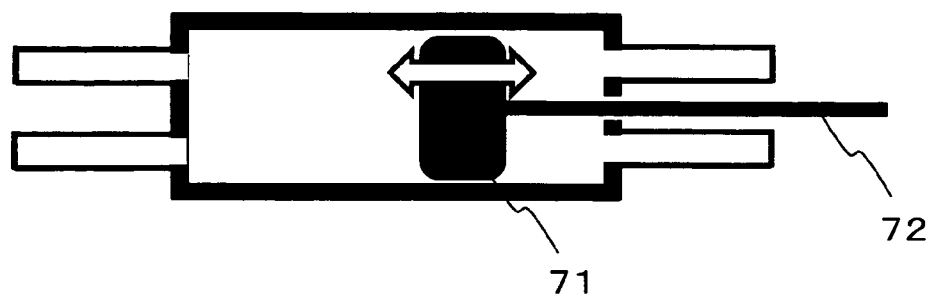
FIG. 9 A schematic view showing a driving mechanism for a slide piston valve used in a reaction control device of the present invention.
Figure 9:
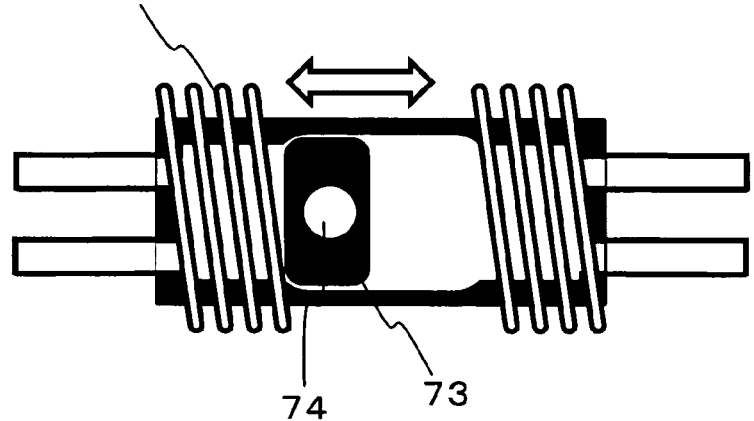
Figure 9:
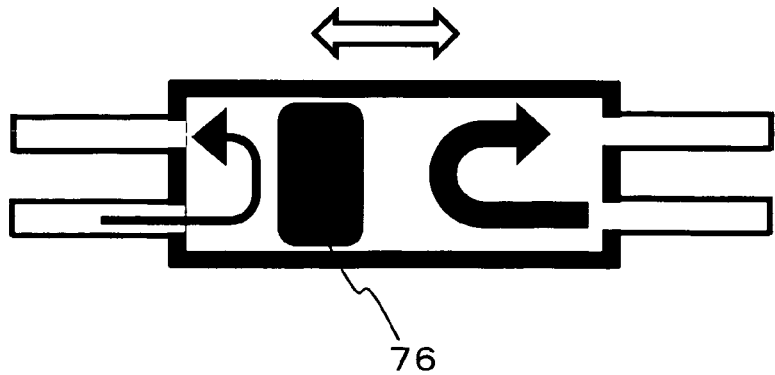

FIG. 9 shows some variations of a driving mechanism of a piston of a piston valve used in a reaction control device of the present invention. According to one method, a piston 71 is integrally formed with a piston rod 72 for direct driving from outside (FIG. 9A). According to other method, a piston 73 is prepared of a ferromagnetic material such as iron or nickel, or a magnet 74 is incorporated inside the piston made of other material. An electromagnetic coil 75 is externally provided to control the current to slide the piston 73 from side to side (FIG. 9B). According to other method, the pressure on the an inlet side or the fluid resistance at the outlet can be controlled to slide the piston 76 from side to side by utilizing difference in the pressures between both sides of the piston 76 (FIG. 9C). Here, the outlined arrows in FIG. 9 indicate the direction of the movement of the piston whereas the solid arrows indicate the direction of the flow of the fluid, where the pointings and the widths of the arrows briefly show the flowing direction and flow rate of the fluid, respectively.

Figure 10:
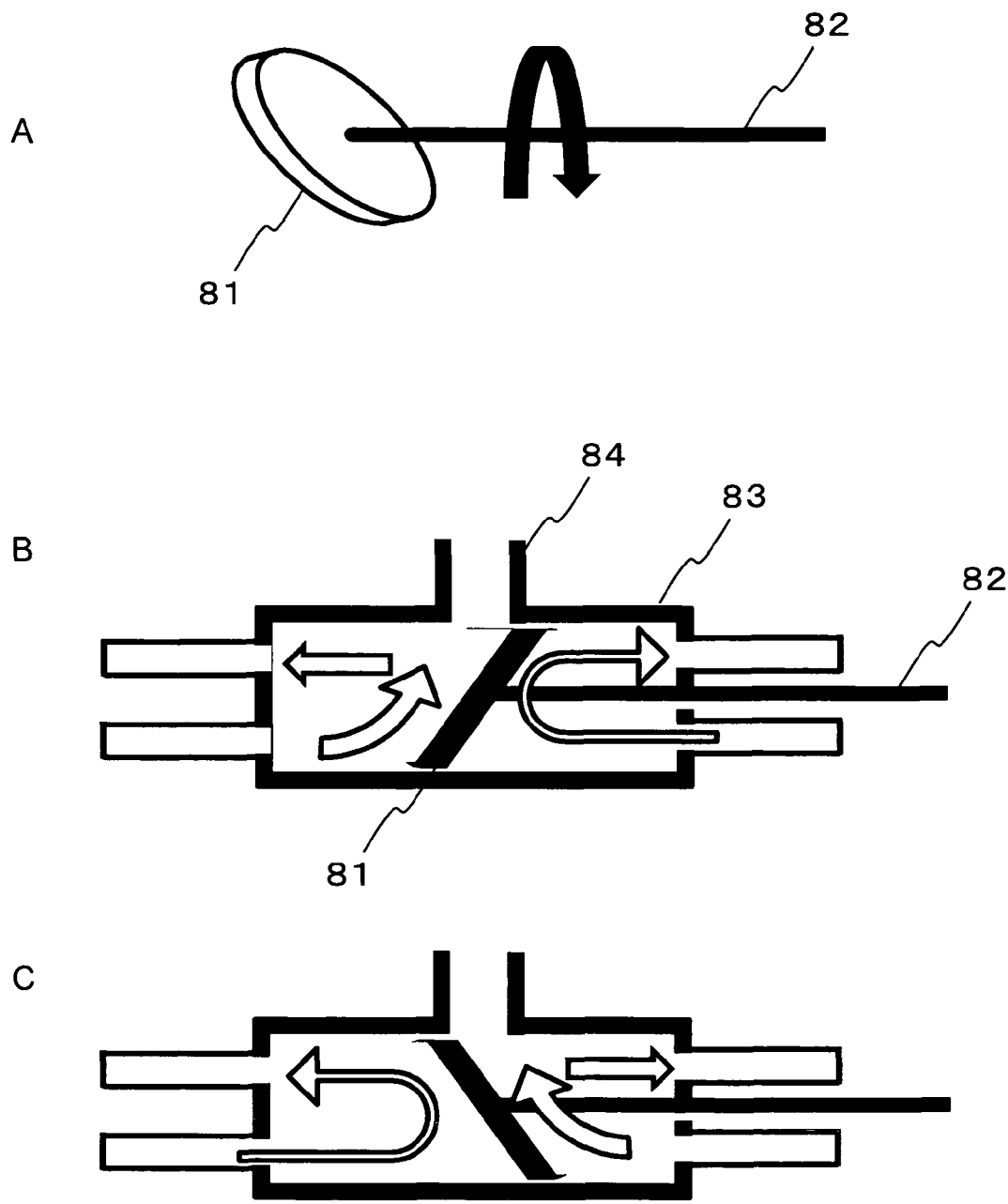
FIG. 10 A schematic view showing a driving mechanism for a rotary valve used in a reaction control device of the present invention.

FIG. 10 shows other embodiment of a switching mechanism of a valve used in a reaction control device of the present invention. A rotary valve 81 made from a slanted oval plate attached to a rod 82 as a rotation axis is inserted inside a circular cross-section heat exchange vessel 83. The rotary valve 81 divides the heat exchange vessel 83 to the right and left, and rotation of the rotation axis 82 can lead a liquid introduced from the right or left side of the heat exchange vessel to the reaction vessel 84. The rotary valve 81 in FIG. 10 has a slanted flat plane shape, other shape such as a spirally wound shape is also possible as long as it gives a similar effect by rotating the rotation axis. Here, the solid arrow in FIG. 10 indicates the rotation direction of the rotation axis 82 while the outlined arrows briefly indicate the flow of the liquids.

Figure 11:
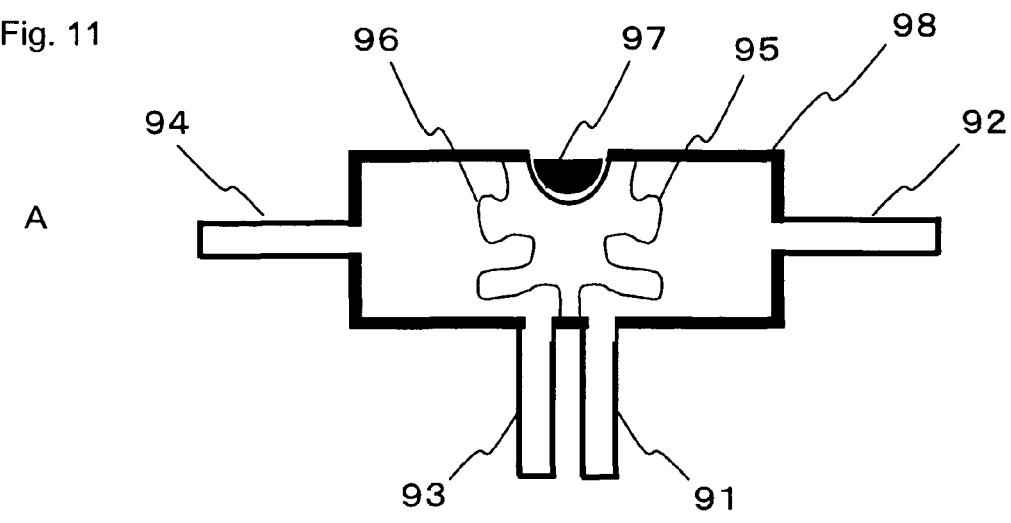
FIG. 11 A schematic view showing a temperature shifting mechanism with a membrane used in a reaction control device of the present invention.
Figure 11:
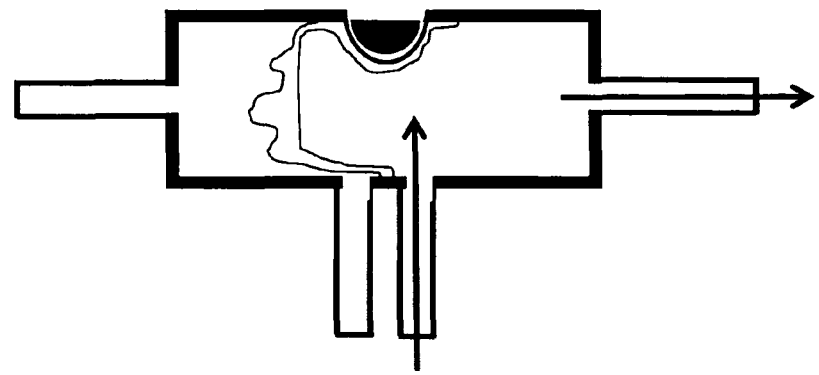
Figure 11:
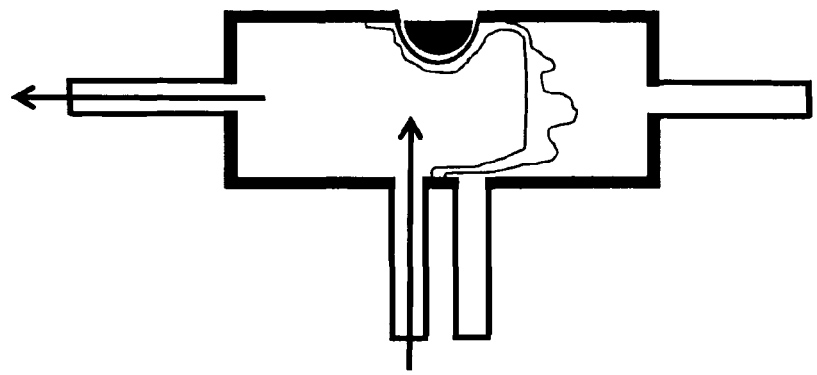

FIG. 11 shows a configuration in which a liquid is replaced with a structure other than a valve. A heat exchange vessel 98 is divided by a membrane A (95) and a membrane B (96). A liquid introduced via an inlet A (91) is discharged outside via an outlet A (92). The presence of the membranes prevents the liquid from being discharged from an inlet B (93) or an outlet B (94) (FIG. 11A). When the pressure of the liquid introduced via the inlet A (91) is higher than the pressure of the liquid introduced via the inlet B (93), the membranes A (95) and B (96) are pushed toward the left side so that the heat of the liquid introduced via the inlet A (91) is conducted to the reaction vessel 97 (FIG. 11B). When the pressure relationship between the liquids introduced from the inlets A (91) and B (93) is reversed, the temperature of the reaction vessel 97 comes to equilibrium with the temperature of the liquid introduced via the inlet B (93) (FIG. 11C). The membranes are preferably prepared from a thin membrane with good heat resistance such as heat-resistant rubber. Here, arrows shown in FIG. 11 briefly indicate the directions of the flow of the liquids.

Figure 12:
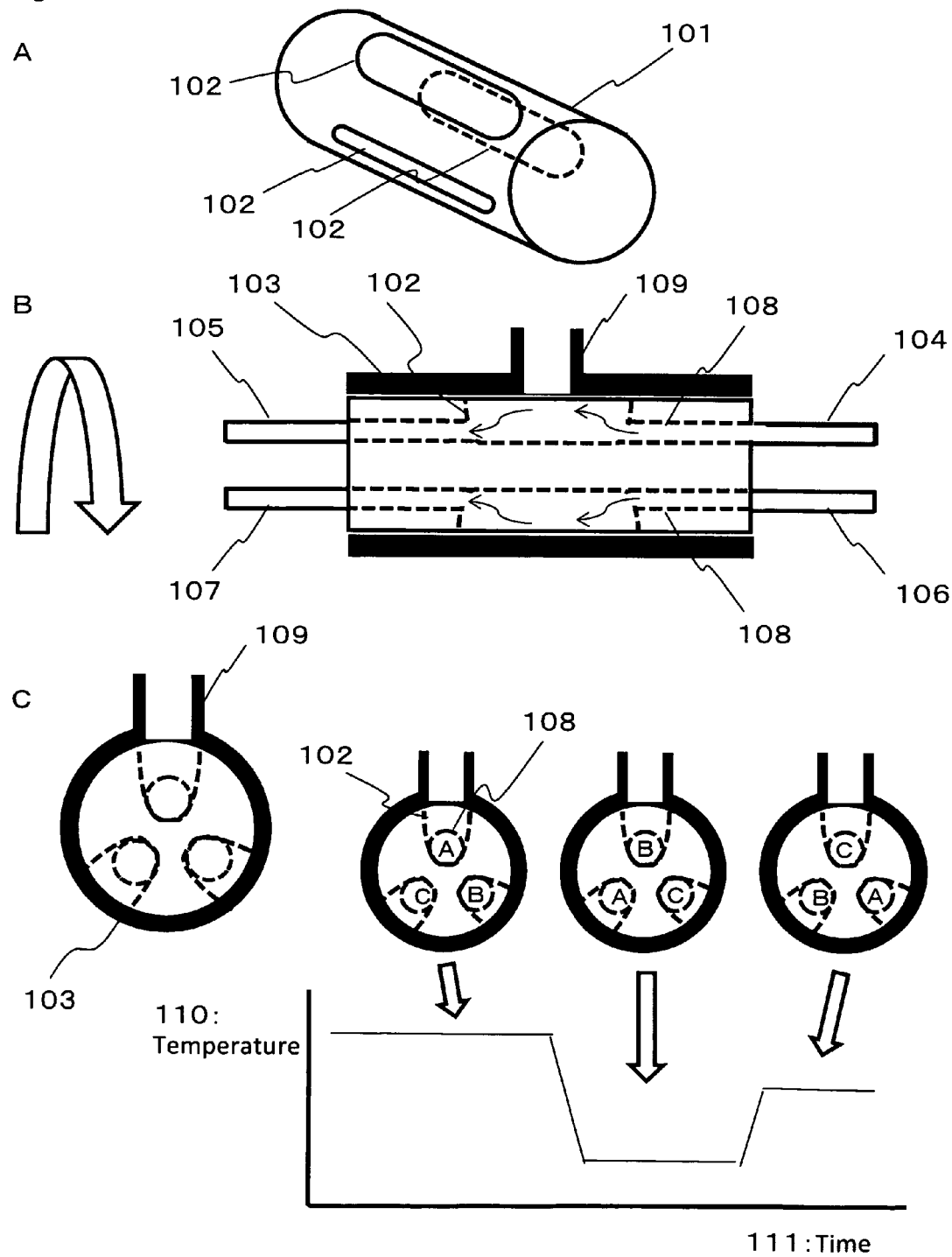
FIG. 12 A schematic view showing a driving mechanism for a temperature-setting valve in a reaction control device of the present invention.

FIG. 12 is a schematic view showing other driving mechanism of a temperature-setting valve used in a reaction control device of the present invention. According to the present invention, the number of temperatures to be set is not limited to two. FIG. 12 shows a configuration of setting three or more temperatures for the reaction vessel. A rotary valve 101 with grooves 102 formed in the side is inserted into a heat exchange vessel 103. Both sides of the rotary valve 101 are provided with an inlet and an outlet. For example, a liquid introduced via an inlet A (104) flows into the grooves 102 via a flow channel 108 to conduct heat to a reaction vessel 109 and then led outside via an outlet A (105). Meanwhile, a liquid introduced via an inlet B (106) is led outside via an outlet B (107) without making contact with a reaction vessel 109. However, a liquid introduced via any inlet can be brought into contact with the reaction vessel by rotating the rotary valve 101 (FIG. 12C). The temperature 110 can be changed as represented by the graph shown in FIG. 12C by rotating the rotary valve 101 with time 111. The rotary valve 101 is preferably prepared from a heat insulating material.

Figure 13:
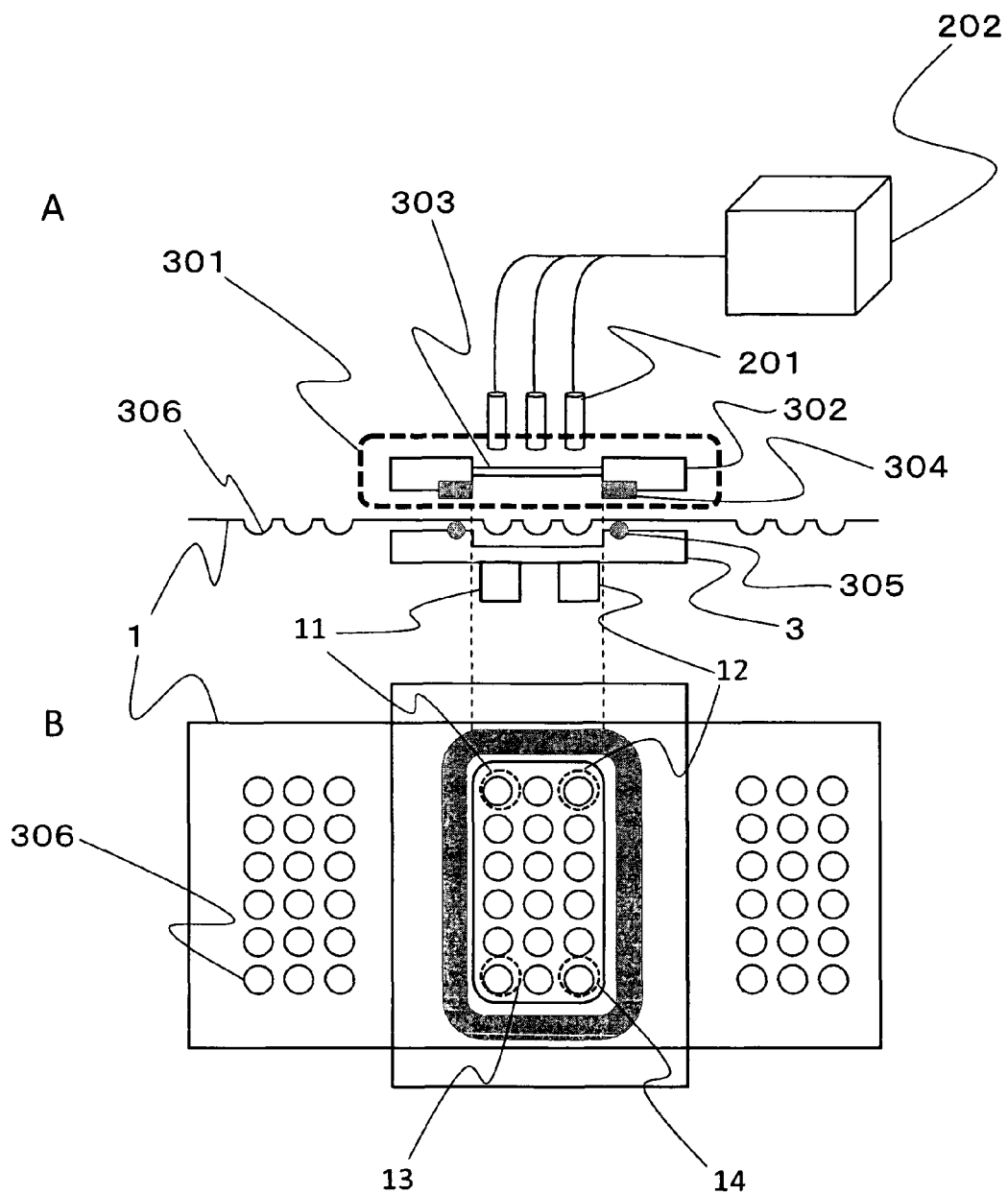
FIG. 13 A schematic view showing an exemplary configuration of a heat exchange vessel used in reaction control device of the present invention.

FIG. 13 is a schematic view showing an exemplary structure of a heat exchange vessel used in a reaction control device of the present invention. The upper panel A shows a lateral view and the lower panel B shows a top view.

With reference to FIG. 13, a reaction vessel 1 is provided with a plurality of concaved wells 306 arranged in arrays for accommodating a sample. A heat exchange vessel 3 is arranged beneath the reaction vessel 1 via an O-ring 305 in contact therewith. The temperature of the reaction vessel 1 is adjusted by a heat exchanging liquid introduced into the heat exchange vessel 3 via inlets A11 and A12. An anti-evaporation mechanism 301 is arranged above the reaction vessel 1 in close contact therewith. This anti-evaporation mechanism 301 prevents the sample solution from evaporating and dissipating due to heating of the sample solution with the heat from the heat exchange vessel 1. Typically, the anti-evaporation mechanism 301 is provided with an adhering member 302, an optically transparent member (e.g., glass heater) 303 and if necessary a polymeric sheet 304. The polymeric sheet 304 can enhance adhesion between the adhering member 302 and the reaction vessel 1. A change in the fluorescent intensity of a sample solution placed in the wells 306 can be detected via the optically transparent member 303 with a fluorescence detector 202 whose operation is controlled with a control analyzer 201.

According to the example shown in FIG. 13, PCR reaction can be carried out by repeating high-speed temperature shift of a small amount of a reaction solution droplet of 1 to 10 microliters mounted on each of the wells 306. First, a reaction vessel 1 having PCR solution droplets mounted thereon is arranged in close contact with a heat exchange vessel 3 via an O-ring 305. The heat exchange vessel 3 is connected to a plurality of inlets for heat exchanging liquids, where two or more heat exchanging liquids at different temperatures are injected from the inlets. According to this example, inlets A 11 and B 12 are shown as an example for heat exchange between two temperatures, but the number of the inlets is not limited thereto. If necessary, three or more inlets can be provided in order to similarly realize three or more different temperatures with the reaction vessel 1.

The optically transparent member 303 on the upper surface of the anti-evaporation mechanism 301 is made from an optically transmissive transparent material such as glass or plastic so that optical characteristics such as change in the fluorescent intensity of the reaction solution droplets in the wells 306 of the reaction vessel 1 can be observed from outside with an optical device such as a fluorescence detector 101. Furthermore, this optically transparent member 303 may be a glass heater obtained by providing a heat generating member made from an optically transparent material such as ITO (Indium Tin Oxide) whose temperature can be increased by running a current on the surface of the above-mentioned optically transparent material to form an integrated body of the optically transparent glass and the heat generating member. Such a glass heater can be used to heat the upper surface of the anti-evaporation mechanism to prevent the PCR solution droplets in the reaction vessel 1 from evaporating.

Accordingly, one exemplary embodiment of the anti-evaporation mechanism 301 comprises a glass heater 303 having an integrated body of an optically transparent glass and a heat generating mechanism, a sealing member 302, and a polymeric sheet 304 that adheres the reaction vessel 1 and the sealing member 302. The reaction vessel 1 can be sandwiched by the anti-evaporation mechanism 301 and the heat exchange vessel 3 so that even when a small amount of reaction solution evaporates, saturated vapor pressure is immediately restored in the space between the reaction vessel 1 and the anti-evaporation mechanism 301. In order to prevent moisture vapor from condensating on the inner wall of the sealing member 302, the glass heater 303 or the like upon reaching saturated vapor pressure, the temperature of the glass heater 303 that is accessible to the outer air can be heated to a range of 80° C. to 110° C., for example, thereby preventing condensation of moisture vapor. In addition, a glass surface heated by the glass heater 303 in this manner has a defogging effect, and thus advantageous in that it does not interfere with detection of the fluorescence intensity of the reaction solution with a fluorescence detector 101.

The sealing performance of the sealing member 301 can be enhanced with a polymeric sheet 304 or the like. Examples of polymeric sheets that can be used include, but not limited to, rubber and silicon.

Since a smaller volume of the space between the anti-evaporation mechanism and the reaction vessel 1 can suppress the total amount of the moisture vapor that reaches the saturated moisture vapor pressure to a smaller amount, the distance between the glass heater 303 and the surface of the reaction vessel 1 is advantageously made as close as possible. The distance between the glass heater 303 and the surface of the reaction vessel 1 is preferably about 10 mm or less, more preferably about 7 mm or less, still more preferably about 5 mm or less, and most preferably about 3 mm or less. According to this example, the glass heater 303 was used as one example of the heating mechanism on the upper surface of the anti-evaporation mechanism 301. Similarly, a metal plate or the like having a heating mechanism or a heat conduction system can be provided with an optically transparent window that allows detection of fluorescence from the droplet with a fluorescence detector 101, to be used in place of the glass heater 303. When an anti-evaporation mechanism is used, evaporation of even a small amount of droplet can be prevented and thus there is no need of layering a liquid layer such as mineral oil above the droplet.

Thus, according to the example shown in FIG. 13, dissipation of the sample solution due to evaporation of the liquid droplet of the reaction vessel caused by heat from the heat exchange vessel 3 can be prevented.

INDUSTRIAL APPLICABILITY

The present invention is useful as a reaction device for carrying out reaction that requires accurate control of the temperature of a sample. The present invention is also useful as a reaction device for carrying out reaction that requires rapid shifting of the sample temperature.

In particular, the present invention is useful as a PCR device capable of carrying out PCR reaction at high speed, high accuracy and high amplification rate. Since a device of the present invention can be downsized, it is also useful as a portable PCR device.

In addition, since the present invention is capable of preventing a sample solution from evaporating due to heating thereof, it is useful for PCR reaction that uses a small amount of sample.

DESCRIPTION OF REFERENCE NUMERALS

1 Reaction vessel
2 Reaction vessel casing
3 Heat exchange vessel
4 Liquid reservoir tank
5 Heat source
6 Stirring mechanism
7 Pump
8 Switching valve
9 Bypass flow channel
10 Auxiliary temperature control mechanism
11 Inlet A
12 Inlet B
13 Outlet A
14 Outlet B
21, 22, 23, 24, 26 Reaction vessel
25 Lyophilized reagent
27 Dispensing chip
28 Sample
29 Fiber ball
31 Reaction vessel
32 Reaction vessel casing
33 Reaction vessel socket
34 Thread
35 Seal
36 Tapered reaction vessel casing
37, 38 Heat exchange vessel
41 Inlet valve A 42 Outlet valve A
43 Inlet valve B
44 Outlet valve B
51 Glass-slide like reaction vessel casing
52, 58 Reaction vessel socket of heat exchange vessel
53 Guide rail
54, 57 Seal
55 Slide socket
56 Hinge
59 Reaction vessel
61 Inlet A
62 Outlet A
63 Inlet B
64 Outlet B
65 Piston
66 Reaction vessel
67 Heat exchange vessel
71 Piston
72 Piston rod
73 Piston
74 Magnet
75 Electromagnetic coil
76 Piston
81 Rotary valve
82 Rotation axis
83 Heat exchange vessel
84 Reaction vessel
91 Inlet A
92 Outlet A
93 Inlet B
94 Outlet B
95 Membrane A
96 Membrane B
97 Reaction vessel
98 Heat exchange vessel
101 Rotary valve
102 Grooves
103 Heat exchange vessel
104 Inlet A
105 Outlet A
106 Inlet B
107 Outlet B
108 Flow channel
109 Reaction vessel
110 Temperature
111 Elapsed time
201 Fluorescence detector
202 Control analyzer
203 Control signal
204 Optical window
301 Anti-evaporation mechanism
302 Sealing member
303 Glass heater
304 Polymeric sheet
305 O-ring
306 Well

The invention claimed is:
1. A liquid reflux reaction control device comprising:
a plurality of liquid reservoir tanks provided with a temperature-controllable heat source for maintaining liquids of predetermined temperatures;
a heat exchange vessel provided in contact with a reaction vessel so as to conduct heat to the reaction vessel, and comprising an inlet and an outlet respectively for introducing and discharging a liquid of a predetermined temperature;
a tubular flow channel that connects the inlet and the outlet of the heat exchange vessel with each of the plurality of the liquid reservoir tanks;
a pump configured to circulate the liquid between the heat exchange vessel and each of the plurality of the liquid reservoir tanks;
wherein the reaction vessel has one or more wells configured to accommodate a sample solution and is detachably arranged on the heat exchange vessel, and the liquid of the predetermined temperature in the heat exchange vessel contacts with the bottom surface of the reaction vessel directly or through a membrane;
a switching mechanism configured to switch, at a predetermined time interval, between (i) liquid of the predetermined temperature from one of the plurality of the liquid reservoir tanks, wherein the liquid in (i) is introduced into and discharged from the heat exchange vessel through one pair of inlet and the outlet and contacts with the bottom surface of the reaction vessel, and (ii) liquid of another predetermined temperature from another one of the plurality of liquid reservoir tanks, wherein the liquid in (ii) is introduced into and discharged from the heat exchange vessel through another pair of the inlet and the outlet and contacts with the bottom surface of the reaction vessel while preventing each of the liquids in (i) and (ii) from mixing together in the heat exchange vessel,
wherein
the reaction vessel is formed of a metal selected from the group consisting of aluminum, nickel, magnesium, titanium, platinum, gold, silver, and copper, or of silicon; has a thickness of 1-100 microns; and is suitable for accommodating an amount of the sample less than or equal to about 0.1 µL to about 100 µL per well;
the total volume of the circulating liquid is more than or equal to several tens of mL per liquid reservoir tank;
the volume of the heat exchange vessel is about 0.01 mL to about 10 mL per well; and
the circulation rate of the liquid is about 1 mL/sec to about 100 mL/sec; and
wherein the switching mechanism comprises:
(I) a switching valve disposed at each of the inlet and the outlet, wherein the one pair of the inlet and the outlet is open, and alternately the other pair of the inlet and the outlet is closed to switch between the liquids while preventing each of the liquids from mixing together in the heat exchange vessel;
(II) a slide piston valve comprising a heat exchange vessel and a piston which is inserted in the heat exchange vessel and capable of occluding an opening when the reaction vessel is displaced from the heat exchange vessel;
(III) a heat exchange vessel having a cylindrical inner space, a rotary valve comprised of an oval plate defining the inner space in two parts, being inserted in the heat exchange vessel and rotatable around an axis that is generally perpendicular to the circular cross-section of the heat exchange vessel and a rod inserted in the heat exchange vessel generally perpendicularly to the circular cross-section of the heat exchange vessel and connected to the rotary valve and functioning as a rotating axis,
wherein the liquids of the predetermined temperatures are introduced into and discharged from each of the divided inner spaces through the one pair of the inlet and the outlet and the other pair of the inlet and the outlet, respectively, such that the liquid which contacts with the bottom surface of the reaction vessel is replaced by the rotary valve by rotating the rotating axis;

(IV) a heat exchange vessel and a membrane arranged to divide the inner space of the heat exchange vessel in two parts such that the liquid introduced into and discharged from the heat exchange vessel through the pair of the inlet and the outlet does not mix with the liquid introduced into and discharged from the heat exchange vessel through the other pair of the inlet and the outlet; or (V) a cylindrical rotor that is rotatably inserted into the heat exchange vessel, wherein said rotor comprises a plurality of grooves formed in its outer surface as flow channels for the liquid delivered from the liquid reservoir tank, and a tunnel-like flow channel connected to each of the grooves to allow fluid communication, wherein both ends of the tunnel-like flow channel serve as an inlet or an outlet of the switching mechanism, and wherein rotation of the rotor allows liquids at different temperatures to be introduced into the inlet to make contact with exterior of the reaction vessel upon passing the groove part.

2. The liquid reflux reaction control device according to claim 1, which is used as a PCR device.

3. The liquid reflux reaction control device according to claim 1, further comprising, where a fluorescent dye is added to the sample solution in the reaction vessel, a fluorescent detector configured to detect fluorescence emitted from the fluorescent dye and to measure fluorescent intensity with time.

4. The liquid reflux reaction control device according to claim 3, wherein the fluorescent detector is disposed in correspondence with each of the wells of the reaction vessel.

5. The liquid reflux reaction control device according to claim 3, further comprising:

a means for estimating the change in a temperature of a sample solution based on the change in the fluorescent intensity of the sample solution in one or a plurality of wells of the reaction vessel; and a means for rapidly shifting the temperature of the reaction vessel based on the result thereof.

6. The liquid reflux reaction control device according to claim 1, wherein the number of the liquid reservoir tanks is the same as the number of temperatures intended for the reaction vessel.

7. The liquid reflux reaction control device according to claim 6, wherein the number of the liquid reservoir tanks is 2 or 3.

8. The liquid reflux reaction control device according to claim 1, wherein the shape of the bottom surface of the well is flat, hemispherical, trigonal pyramid shape or spherical.

9. The liquid reflux reaction control device according to claim 1, wherein a reagent necessary for the reaction is accommodated in each of the wells in a dry form in advance such that it eluted and brought into reaction upon contacting with the sample solution.

10. The liquid reflux reaction control device according to claim 1, wherein the reaction vessel further comprises an aperture or an optical window through which measurement of optical signals from the sample of the reaction vessel is made.

11. The liquid reflux reaction control device according to claim 1, wherein the reaction vessel is provided in a removable manner with respect to the heat exchange vessel in one of the following fashion: (a) a cylindrical casing is provided surrounding the reaction vessel, and a cylindrical reaction vessel socket is provided on the heat exchange vessel, while the outer surface of the casing of the reaction vessel and the inner surface of the reaction vessel socket of the heat exchange vessel are threaded so that the reaction vessel is removably attached to the heat exchange vessel through rotation movement along the thread; (b) a cylindrical casing surrounding the reaction vessel and a cylindrical reaction vessel socket of the heat exchange vessel are tapered with respect to each other so as to be removably attached to each other by pressing the reaction vessel against the reaction vessel socket; (c) the reaction vessel is secured to a glass-slide like reaction vessel casing while the reaction vessel socket of the heat exchange vessel is provided with a guide rail so that the glass-slide like reaction vessel casing is removably attached to the socket along the guide rail; and (d) the glass-slide like reaction vessel casing is inserted into a slide holder with a hinge mechanism so that the glass-slide like reaction vessel casing is removably attached to the reaction vessel socket of the heat exchange vessel through rotation movement of the hinge mechanism.

12. The liquid reflux reaction control device according to claim 1, further comprising a mechanism configured to allow the reaction vessel to attach to or remove from the heat exchange vessel during reflux of the liquid without leaking the liquid out from the liquid reflux reaction control device.

13. The liquid reflux reaction control device according to claim 1, wherein the plurality of the liquid reservoir tanks is provided with a heat source, a thermometer, and a liquid stirrer, wherein the liquid stirrer is provided with a heat source controller configured to control the temperature distribution of the liquid in the liquid reservoir tank within 5° C. by stirring the liquid in the liquid reservoir tank continuously or at a duty cycle ratio of 10% or higher.

14. The liquid reflux reaction control device according to claim 1, further comprising a controller configured to control the switching mechanism.

15. The liquid reflux reaction control system according to claim 1, wherein the switching mechanism is configured to lead the liquid in any liquid reservoir tank among the plurality of liquid reservoir tanks to the heat exchange vessel and to return the liquid in the heat exchange vessel to the original liquid reservoir tank.

16. The liquid reflux reaction control device according to claim 14, wherein, when the liquid in the heat exchange vessel is replaced by controlling the switching mechanism, the switching mechanism is controlled such that the liquid in the heat exchange vessel is led to a liquid reservoir tank maintained at a temperature closest to the temperature of the liquid.

17. The liquid reflux reaction control device according to claim 1, further comprising an auxiliary temperature control mechanism comprising a thermal insulator, a heater, and a cooling mechanism, wherein the auxiliary temperature control mechanism is configured to suppress the fluctuation of the temperature of the liquid in the flow channel that connects the switching mechanism to the plurality of liquid reservoir tanks.

18. The liquid reflux reaction control device according to claim 1, further comprising in the switching mechanism a mechanism configured to control the shift in the temperature by continuously replacing the liquid from the liquid reservoir tank regardless of whether or not the liquid in the flow channel connecting the switching mechanism to the plurality of liquid reservoir tanks is led to the heat exchange vessel.

19. The liquid reflux reaction control device according to claim 1, wherein the switching mechanism comprises a piston configured to slide in a hollow structure having a circular or polygonal cross-section so as to control the temperature of the liquid that is in contact with the reaction vessel according to the position of the piston.

20. The liquid reflux reaction control device according to claim 19, wherein the piston in the switching mechanism is configured to slide by:
   (a) mechanically applying external force to the piston rod connected to the piston;
   (b) using a piston that is a magnetic body itself or a piston mounted with a magnetic body inside to utilize interaction between the piston and a magnetic field generation mechanism including an electromagnetic coil arranged outside the switching mechanism; or
   (c) generating difference in pressure due to the flow of the liquids circulating at both ends of the piston.

21. The liquid reflux reaction control device according to claim 1, wherein the circulating liquid used is a liquid ammonia.

22. The liquid reflux reaction control device according to claim 1, wherein the circulating liquid used is a liquid having a boiling point higher than that of water.

23. The liquid reflux reaction control device according to claim 1, wherein the circulating liquid used is a liquid having a freezing point lower than that of water.

24. The liquid reflux reaction control device according to claim 1, further comprising a mechanism configured to prevent the sample from evaporating, the mechanism comprising:
   a member that sealingly covers the surface of the reaction vessel having the well, such that at least part of it is optically transparent so as to allow optical observation of the sample solution in the well; and
   a heating mechanism configured to heat a part of the optically transparent part of the member.

25. The liquid reflux reaction control device according to claim 24, wherein the distance between the optically transparent part of the member and the surface of the reaction vessel having the well is less than or equal to 3 mm.

26. The liquid reflux reaction control device according to claim 24, wherein the temperature of the optically transparent part of the member is heated with the heating mechanism in a range of 80° C. to 110° C.

27. The liquid reflux reaction control device according to claim 1, wherein the sample solution contains nucleic acids and a DNA polymerase.

* * * * *